United States Patent
Shimodaira et al.

[11] Patent Number: 5,967,782
[45] Date of Patent: Oct. 19, 1999

[54] ARTIFICIAL DENTAL IMPLANT

[75] Inventors: Kenichi Shimodaira; Junichi Hayashi; Michio Ito, all of Nagano-ken, Japan

[73] Assignees: Injex Coporation, Nagano-kun; Matsumoto Dental College, Nagano-ken, both of Japan

[21] Appl. No.: 08/900,701

[22] Filed: Jul. 25, 1997

[30] Foreign Application Priority Data

Jul. 25, 1996 [JP] Japan ................................ 8-196784

[51] Int. Cl.⁶ ........................................ A61C 8/00
[52] U.S. Cl. ........................................ 433/173; 433/201.1
[58] Field of Search .................................. 433/172, 173, 433/174, 175, 176, 201.1; 623/11; 606/16, 18

[56] References Cited

U.S. PATENT DOCUMENTS

| | | | |
|---|---|---|---|
| 5,174,755 | 12/1992 | Fukuda | 433/173 |
| 5,205,746 | 4/1993 | Chanavaz | 433/174 |
| 5,344,457 | 9/1994 | Pilliar et al. | 433/174 X |
| 5,642,996 | 7/1997 | Mochida et al. | 433/174 |
| 5,717,006 | 2/1998 | Daculsi et al. | 623/11 X |

FOREIGN PATENT DOCUMENTS

| | | |
|---|---|---|
| 0 214 341 | 3/1987 | European Pat. Off. . |
| 0 405 556 | 1/1991 | European Pat. Off. . |
| 0 664 998 | 8/1995 | European Pat. Off. . |
| 4-105659 | 4/1992 | Japan . |
| 5-220177 | 8/1993 | Japan . |

*Primary Examiner*—Nicholas D. Lucchesi
*Attorney, Agent, or Firm*—Hill & Simpson

[57] ABSTRACT

An artificial dental implant includes an implanting part which is to be implanted in bone tissue and a crown-fixing part to which a crown is to be fixed, which are manufactured using a metal powder injection molding method. At least a part of a portion of said implanting part which defines an outer surface thereof is formed with a metal material which contains Ti as a base material and 0.01 to 3 wt % of M (where M is at least one selected from the group comprising Ca, P and Si). Further, the implanting part preferably has a coating layer which covers the outer surface thereof, in which the M content (where M is at least one selected from the group comprising Ca, P and Si) in this coating layer is preferably greater than the M content in the at least a part of the portion of the implanting part. The implanting part and crown-fixing part may be formed into an integral body, or formed into separate bodies such that they are engaged with each other when used. The artificial dental implant having the structure described above is easy to manufacture and has good bio-affinity and high strength.

21 Claims, 5 Drawing Sheets

ARTIFICIAL DENTAL IMPLANT

BACKGROUND OF THE INVENTION

1. Field of Invention

This invention relates to an artificial dental implant.

2. Description of the Prior Art

There are known artificial dental implants which can be used in place of the roots of natural teeth. An artificial dental implant is constructed with an implanted part (fixture) which is to be implanted in the bone tissue and a crown-fixing part (abutment screw) to which a crown is to be fixed.

As for materials for forming such artificial dental implants, (1) metals such as stainless steel and Ti (titanium) and the like, and (2) ceramics such as zirconia-based, alumina-based and sapphire-based ceramics are conventionally used.

However, artificial dental implants formed from ceramics have the disadvantage of low strengths, and therefore they are likely to be easily damaged. Moreover, ceramic artificial dental implants are very expensive.

Consequently, attention has focused on metal artificial dental implants with which there are fewer disadvantages described above. Such metal artificial dental implants are usually made by means of casting and a machining process performed after the casting process.

Among the metal artificial dental implants, stainless steel artificial dental implants have poor bio-compatibility, so that they have adverse effects on the body such as causing the onset of metal allergy and the risk of cancer resulting from the dissolution of Ni and Cr.

On the other hand titanium (Ti) artificial dental implants are relatively light and have high strength, and they have excellent corrosion resistance and bio-compatibility.

However, in the case of Ti artificial dental implants, cutting processes using special tools and laser working must be carried out on the castings or ultra-plastic mold processing is required, to manufacture and process them, thus resulting in a problem in that production is not easy. In particular, a complicated manufacturing process and a high degree of skill are required to process the castings into complicated and fine shapes, so that the manufacturing costs are also increased.

Further, the bio-compatibility of Ti itself is not so excellent. Consequently, in Ti artificial dental implants, there is a case that a long time is required after they are implanted in the patient's bone tissue until they become fixed with the bone tissue. Accordingly, depending on the particular case, there is a case that the artificial dental implant which has been implanted in the bone tissue is fall out.

SUMMARY OF THE INVENTION

The object of the present invention is to provide artificial dental implants which are easy to manufacture and have good bio-compatibility and high strength.

In order to achieve the object, the present invention is directed to an artificial dental implant which comprises an implanting part which is to be implanted in bone tissue, that implanting part having a portion defining an outer surface thereof; and a crown-fixing part to which a crown is to be fixed; wherein both that implanting part and that crown-fixing part are manufactured using a metal powder injection molding method, and at least a part of that portion of that implanting part is formed with a metal material which contains Ti as a main component and 0.01 to 3 wt % of M (where M is at least one selected from the group comprising Ca, P and Si).

Further, in order to achieve the object, the present invention is also directed to an artificial dental implant which comprises an implanting part which is to be implanted in bone tissue and which is manufactured using a metal powder injection molding method, that implanting part having a portion defining an outer surface thereof; and a crown-fixing part to which a crown is to be fixed and which is manufactured using the metal powder injection molding method, that crown-fixing part adapted to be engaged with that implanting part when used, wherein at least a part of that portion of that implanting part is formed with a metal material which contains Ti as a main component and 0.01 to 3 wt % of M (where M is at least one selected from the group comprising Ca, P and Si).

Furthermore, in order to achieve the object, the present invention is also directed to an artificial dental implant which comprises an implanting part which is to be implanted in bone tissue and which is manufactured using a metal powder injection molding method, that implanting part having a portion defining an outer surface thereof, in which at least a part of that portion of that implanting part being formed with a metal material which contains Ti as a main component and 0.01 to 3 wt % of M (where M is at least one selected from the group comprising Ca, P and Si); and a crown-fixing part to which a crown is to be fixed and which is manufactured using the metal powder injection molding method, that crown-fixing part adapted to be engaged with that implanting part when used, wherein the porosity of that implanting part is higher than the porosity of that crown-fixing part, and the M content of that implanting part is greater than the M content (where M is at least one selected from the group comprising Ca, P and Si) of that crown-fixing part.

In these cases, it is preferred that at least a part of the portion of the implanting part includes 0.01 to 1 wt % of Ca, 0.01 to 0.5 wt % of P, or 0.01 to 0.5 wt % of Si.

In this way, it becomes possible to improve bio-affinity of the artificial dental implant further with maintaining sufficient strength and hardness of the metal material from which the artificial dental implant is being formed.

Further, it is also preferred that the porosity of the implanting part is from 5 to 15 vol %.

If pores are formed in the vicinity of the surface of the metal material from which the artificial dental implant is formed, formation of bone tissue becomes easy since tissue fluid necessary for the growth of bone tissue is promoted. Further, bonding strength of the bone tissue to the artificial dental implant is improved since the presence of pores increases the surface area. Further, loosening or shedding of the implanting part can be suppressed with maintaining the strength and hardness of the implanting part.

Furthermore, it is also preferred that the porosity of the crown-fixing part is equal to or less than 3 vol %.

In this way, it becomes possible to improve the strength and hardness of the crown-fixing part and to suppress the entry of saliva and micro-organisms into the crown-fixing part 2.

Moreover, it is also preferred that at least the implanting part has a coating layer which covers the outer surface thereof, and the coating layer is formed at a metal material containing M (where M is at least one selected from the group comprising Ca, P and Si).

By providing such a coating layer onto the implanting part, it becomes possible to improve the bio-affinity of the artificial dental implant. In practical terms, if such a coating layer is formed on the implanting part, the bone tissue will adhere around the implanting part, and then grow, and thereby the implanting part will be fixed by this bone tissue. Further, if a coating layer is formed on the crown-fixing part, the crown-fixing part exhibits an excellent bio-affinity for gum tissue.

Moreover, the coating layer may be a porous material film. With such a structure, the tissue fluid moistening, which is required for the regeneration of bone, is promoted and the formation of bone tissue around the artificial dental implant can be achieved easily. Furthermore, since bone tissue can enter into the pores, the implanting part can be fixed even more tightly.

In this case, it is further preferred that the M content (where M is at least one selected from the group comprising Ca, P and Si) in the coating layer is greater than the M content in the at least a part of the portion of the implanting part.

By constructing the artificial dental implant in this way, it becomes possible to improve bio-affinity of the artificial dental implant further. Moreover, since M is contained in both the coating layer and the portion of the implanting part, the adhesion between them is further improved.

Other objects, structures and advantages of the present inventions will be apparent when the following description of the preferred embodiments are considered taken in conjunction with the accompanying drawings.

DETAILED DESCRIPTION OF THE PREFERRED EMBODIMENTS

Hereinbelow, preferred embodiments of the artificial dental implants according to the present invention will be described in detail with reference to the accompanying drawings.

Figure 1:
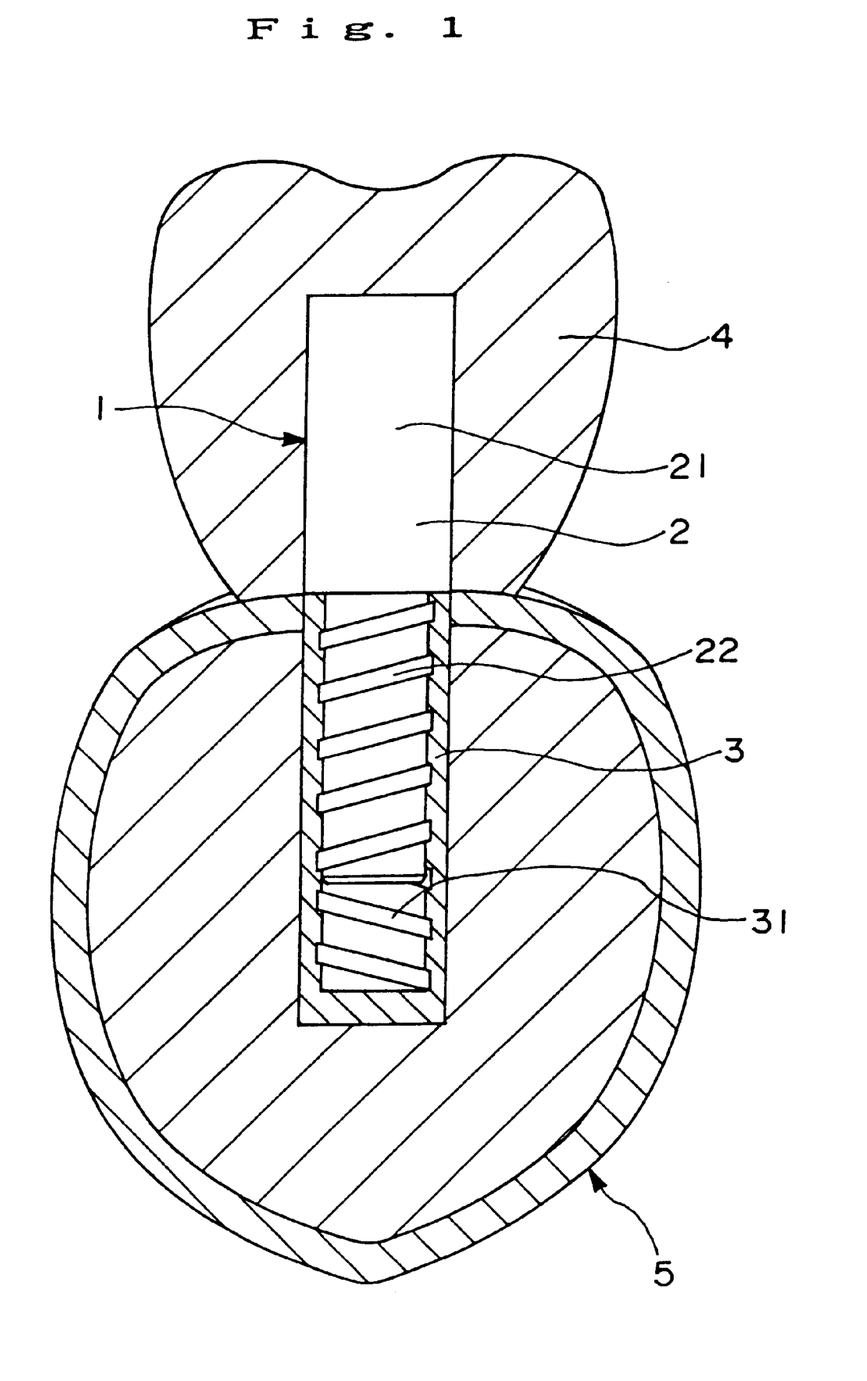
FIG. 1 is a cross sectional view which shows an example of the structure when an artificial dental implant according to the present invention is used as a cylinder-type artificial dental implant.
Figure 2:
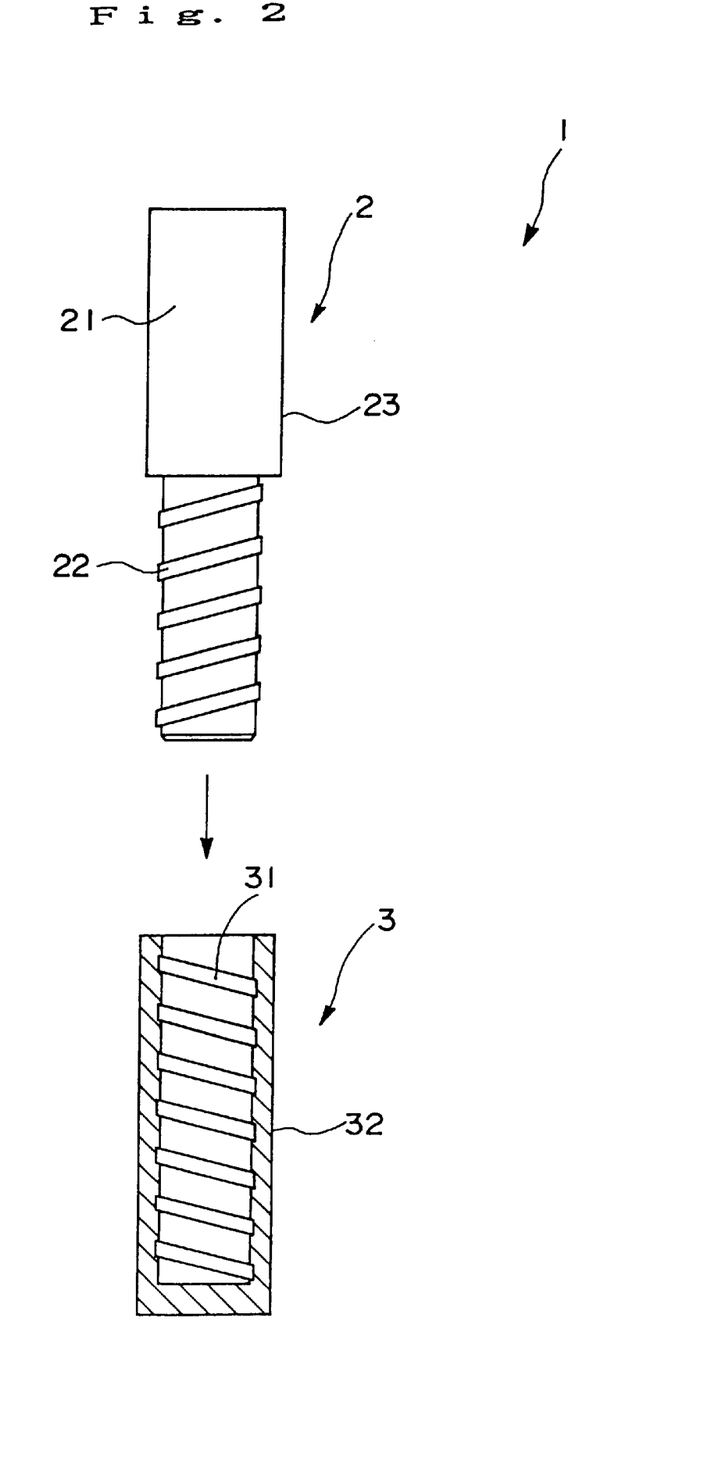
FIG. 2 is a cross sectional view which shows an example of the structure when an artificial dental implant of this invention is embodied as a cylinder-type artificial dental implant.

FIGS. 1 and 2 are cross sectional views which show an example of the construction when an artificial dental implant of this invention is applied to a cylinder-type (screw-in type) artificial dental implant.

As shown in these drawings, the artificial dental implant 1 is formed with an implanting part (fixture) 3 which is to be implanted in the bone tissue and a crown-fixing part (abutment screw) 2 to which the crown, that is the artificial crown (or bridge or the like) 4, is to be fixed.

The crown-fixing part 2 has a cylindrical head part 21 to which the crown 4 is to be fixed and a screw (male thread) 22 which is formed on the end of the head part 21 (the lower side in FIG. 1 and FIG. 2). The crown 4 is fixed on the head part 21 of the crown-fixing part 2 by means of an adhesive or the like.

The implanting part 3 is formed into a cylindrical shape having a bottom. On the inner side of the implanting part 3, there is formed a female thread (screw) 31 into which the thread 22 of the crown-fixing part 2 is to be screwed.

In this connection, the outer surface 23 of the head part 21 of the crown-fixing part 2 and the outer surface 32 of the implanting part 3 are constructed so as to form a continuous surface, when the crown-fixing part 2 and the implanting part 3 are joined together.

When the-artificial dental implant 1 is being fitted to a patient, a hole is formed at the prescribed position in the bone 5 and the implanting part 3 is inserted into this hole, as shown in FIG. 1. That is to say, the implanting part 3 is implanted in the bone tissue. In this state, with the lapse of the prescribed period of time, bone tissue surrounds the outside of the implanting part 3, that is to say that the bone tissue adheres to the implanting part 3, and then the implanting part 3 is fixed by this bone tissue.

Subsequently, the thread 22 of the crown-fixing part 2 is screwed into the thread 31 of the implanting part 3, so that the crown-fixing part is fixed to the implanting part 3.

An artificial dental implant 1 of this type, that is the crown-fixing part 2 and the implanting part 3, is formed from a metal which contains Ti as the base component and 0.01 to 3 wt % of M (where M is at least one metal selected from the group comprising Ca, P and Si).

Since Ti is light and has a high strength and hardness, it is not liable to be deformed or broken. Therefore, an artificial dental implant formed of Ti has excellent durability and corrosion resistance. Further, since Ti has a property that is very little dissolution of the metal component, Ti exhibits excellent bio-compatibility, so that the onset of metal allergy is suppressed.

In the metal material from which the artificial dental implant is formed (hereinafter, referred to simply as the "metal material"), M, that is at least one selected from the group comprising Ca, P and Si, is present in the form of a compound with Ti, for example. The inclusion of the aforementioned elements in the metal material improves the affinity, that is the bio-affinity (bio-compatibility) of the artificial dental implant 1 in respect of bone tissue and gum tissue.

In more practical terms, when M is included in the metal material from which the implanting part 3 is made, bone forming cells are likely to be attached to the M located at the surface of the implanting part, and then bone tissue grows from the attached portions to obtain a state where the Ca, P etc. in the bone tissue is chemically bonded with the metal material at the locations. Accordingly, the bone tissue adheres around the implanting part 3 and grows, and thereby the implanting part 3 is fixed by means of this bone tissue. Furthermore, if M is included in the metal material from which the crown-fixing part 2 is made, the affinity of the crown-fixing part 2 with respect to gum tissue is improved.

In this case, the M content in the metal material is determined to be 0.01 to 3 wt %, preferably 0.03 to 2 wt %, and most desirably 0.05 to 0.5 wt %.

If the M content in the metal material is less than 0.01 wt %, the improving effect on the bio-affinity of the metal material is slight. On the other hand, if the M content exceeds 3 wt %, the strength and hardness of the metal materials is reduced.

Here, it should be noted that the inclusion of Ca in the metal material is preferred, the inclusion of Ca and P (or Si) is more preferred and the inclusion of Ca, P and Si is most preferred.

Ca exhibits a marked effect by improving the bio-affinity of the metal material, even if inclusion thereof is in a trace amount.

If P or Si is included as well as the Ca, then the bio-affinity of the metal material is further improved, and if P and Si are included as well as Ca, then the bio-affinity of the metal material is even further improved.

The Ca content in the metal material is preferably 0.01 to 1 wt %, more preferably 0.02 to 0.5 wt %, and most preferably 0.03 to 0.1 wt %.

In this case, if the Ca content is less than 0.01 wt %, then, in a case where the P and Si content is low, the bio-affinity of the metal material is reduced. On the other hand, if the Ca content exceeds 1 wt %, the strength and hardness of the metal material are reduced.

The P content in the metal material is preferably 0.01 to 0.5 wt %, more preferably 0.02 to 0.3 wt %, and most preferably 0.03 to 0.1 wt %.

If the P content is less than 0.01 wt %, then, in a case where the Ca and Si content is low, the bio-affinity of the metal material is reduced. On the other hand, if the P content exceeds 0.5 wt %, the strength and hardness of the metal material are reduced.

The Si content in the metal material is preferably 0.01 to 0.5 wt %, more preferably 0.02 to 0.3 wt %, and most preferably 0.03 to 0.1 wt %.

If the Si content is less than 0.01 wt %, then, in a case where the Ca and P content is low, the bio-affinity of the metal material is reduced. On the other hand, if the Si content exceeds 0.5 wt %, the strength and hardness of the metal material are reduced.

Furthermore, the M content of the metal material of the implanting part 3 is preferably higher than the M content of the metal material of the crown-fixing part 2. In this way, the bio-affinity of the metal material of the implanting part 3 is further improved.

Furthermore, other elements, such as Fe, Cr, Pd, Co, Zr, Al, V and Mo for example, may be included unavoidably or intentionally in the metal material within the ranges where they cause no harmful effects such as metal allergy. The addition of these elements contributes to increasing the strength of the metal material. These elements may be present in the form of a metal oxide or an Ti-alloy or intermetallic compound with Ti.

Furthers it is preferred that the porosity of the implanting part 3 is higher than that of the crown-fixing part 2.

If pores are formed in the vicinity of the surface of the implanting part 3, the growth of bone tissue is promoted, so that the bone tissue which grows easily enters into the pores and adheres to the inner walls of the pores, which results in that the implanting part 3 is fixed more tightly. In other words, the presence of pores increases the surface area, thereby increasing the bonding strength of the bone tissue against the implanting part.

Hence, if the porosity of the implanting part 3 is comparatively high, the attachment of bone tissue to the implanting part 3 is facilitated, so that loosening or shedding of the implanting part 3 can be suppressed. With this result, the implanting part 3 is fixed more reliably by the bone tissue.

Furthermore, a similar effect to that indicated above can be achieved by increasing the surface roughness of the outer surface of the implanting part 3 to a certain extent. In this regard, it is preferred that the surface roughness Ra, which is defined by the Japanese Industry Standard (JIS) B0601, of the outer surface of the implanting part 3 is 10 to 100 $\mu$m, and more preferable 15 to 50 $\mu$m.

If the surface roughness Ra is too great, then the strength of the implanting part 3 is reduced, while if it is too low, then the aforementioned improving effect is not realized.

On the other hand, if the porosity of the crown-fixing part 2 is made comparatively low, that is if the crown-fixing part 2 is made more dense, then the strength and hardness of the crown-fixing part 2 are increased, thereby the reliability of the artificial dental implant 1 is improved. Furthermore, the entry of saliva and micro-organisms into the crown-fixing part 2 can also be suppressed.

In this regard, it is preferred that the porosity of the implanting part 3 is 5 to 15 vol %, and more preferred 7 to 13 vol %.

If the porosity of the implanting part 3 is less than 5 vol %, then, depending on the average pore size, the effect of preventing the loosening or shedding of the implanted part 3 by means of the pores and bone structure as described above is reduced. On the other hand, if it exceeds 15 vol %, the strength and hardness of the implanted part 3 is reduced.

Further, it is preferred that the porosity of the crown-fixing part 2 is not more than 3 vol %,. and more preferred not more than 2 vol %.

If the porosity of the crown-fixing part 2 exceeds 3 vol %, the strength and hardness of the crown-fixing part 2 is reduced.

Furthermore, it is preferred that the average size (diameter) of the pores in the implanting part 3 is from 5 to 100 $\mu$m, and more preferred 10 to 50 $\mu$m.

If the average size of the pores in the implanting part 3 is less than 5 $\mu$m, that is in a case where the porosity is low, it is difficult for bone tissue to enter the pores (holes), so that the effect of preventing loosening or shedding of the implanting part 3 by means of the pores and bone tissue as described above is reduced. On the other hand, if it exceeds 100 $\mu$m, that is in a case where the porosity is high, the strength and hardness of the implanting part 3 are reduced.

Furthermore, the average size (diameter) of the pores of the crown-fixing part 2 is preferably 0.5 to 50 $\mu$m, and more preferably 5 to 20 $\mu$m.

In this invention, the artificial dental implants 1 are manufactured using the metal powder injection molding method described hereinafter and so pores of this size can be formed easily. In this case, the various conditions concerning the above-mentioned pores can be controlled suitably by setting the manufacturing conditions, such as the type and amount of binder which is to be added and the sintering conditions (for example, the sintering temperature, the sintering time, and the degree of pressure and the gas composition in the sintering environment or the like).

Figure 3:
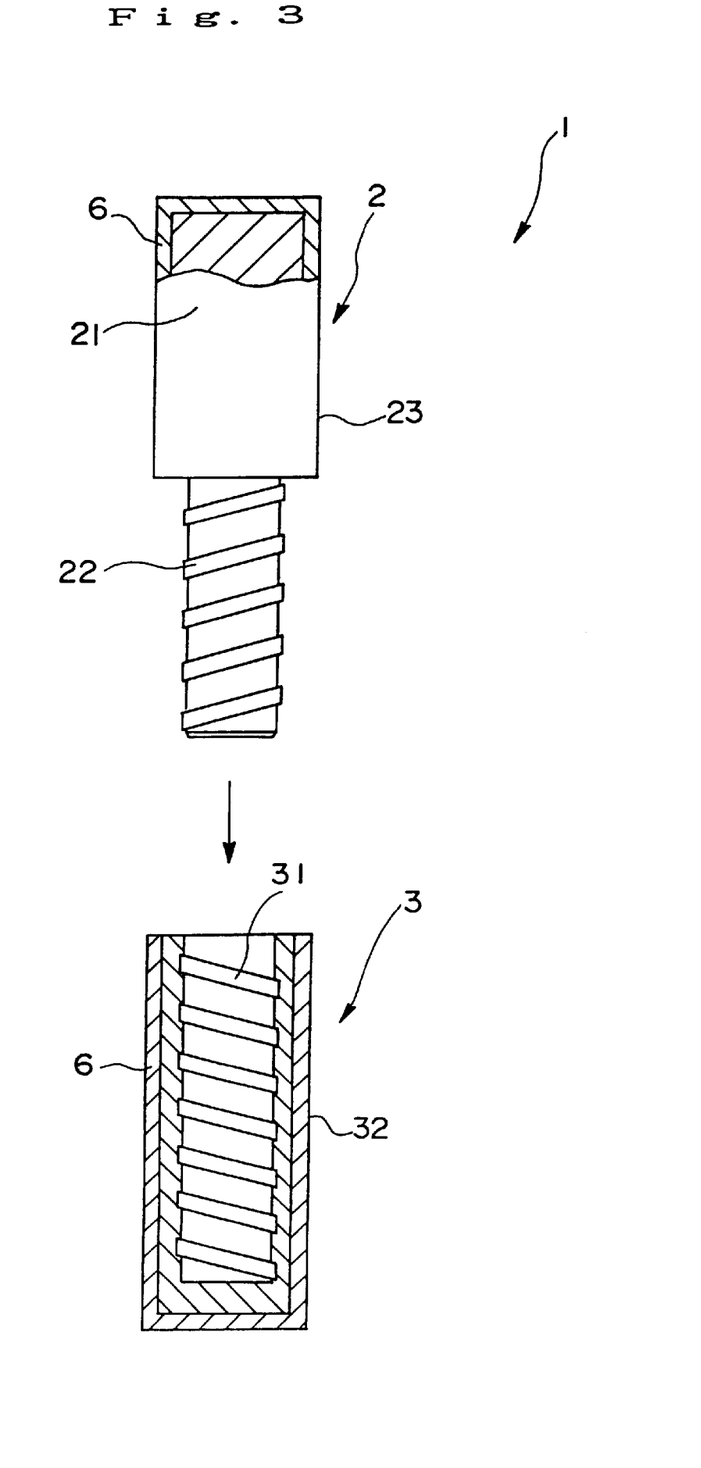
FIG. 3 is a cross sectional view which shows another example of the structure when an artificial dental implant of this invention is embodied as a cylinder-type artificial dental implant.

Further, as shown in FIG. 3, an artificial dental implant 1 of this invention may have a coating layer 6 which covers the outer surfaces of both the crown-fixing part 2 and the implanting part 3.

In this regard, it is preferred that the coating layer 6 contains M therein. In this case, the coating layer 6 can be formed with M, or with a compound of M such as a metal oxide of M.

In this case, it is preferred that the M content in the coating layer 6 on the crown-fixing part 2 is greater than the M content at a portion close to or defining the outer surface of the crown-fixing part 2.

Further, it is preferred that the M content in the coating layer 6 on the implanting part 3 is greater than the M content at a portion close to or defining the outer surface of the implanting part 3.

By providing such an M-rich coating layer 6, it becomes possible to improve the bio-affinity of the artificial dental implant 1. In practical terms, if a coating layer 6 is provided onto the implanting part 3, then the bone tissue will adhere around the implanting part 3 reliably and in a short period of time, and then grow, and thereby the implanting part 3 will be fixed by this bone tissue. Moreover, if a coating layer 6 is formed on the crown-fixing part 2, then the crown-fixing part 2 has an excellent affinity for gum tissue. Furthermore, since M is included in both the coating layer 6 and the metal material, the adhesion between the coating layer 6 and the metal material is also improved.

Moreover, the coating layer 6 may be a porous material film. With such a structure, the tissue fluid moistening, which is required for the regeneration of bone, is promoted and the formation of bone tissue around the artificial dental implant can be achieved easily. Furthermore, since bone tissue can enter into the pores, the implanting part 3 can be fixed even more tightly as a result.

The thickness of the coating layer 6 is preferably not more than 200 $\mu$m, more preferably 10 to 100 $\mu$m, and most preferably 50 to 80 $\mu$m.

If the thickness of the coating layer 6 exceeds 200 $\mu$m, then the strength of the coating layer itself is reduced.

In this connection, it should be noted that a description of the structure other than the coating layer 6 is omitted, since it is the same as that of the artificial dental implant 1 described above on which no coating layer 6 was formed.

The artificial dental implants as described above are manufactured by means of a metal powder injection molding (MIM: Metal Injection Molding). Therefore, hereinbelow, a description is made with reference to the Metal Injection Molding.

(1) A metal powder comprising titanium or a titanium alloy, a powder of the metal material M or M compound and a binder (organic binder) are prepared, and these ingredients are mixed or kneaded by a kneading machine to obtain a compound.

The mean grain diameter of the metal powder is not subject to any particular limitations. However, in normal cases, the diameter is preferably set to about 5 to 60 $\mu$m, and more preferably set to about 10–40 $\mu$m.

Further, the mean grain diameter of M or M compound is not also subject to any particular limitations. However, in normal cases, the diameter is preferably set to about 1 to 20 $\mu$m, and more preferably set to about 5 to 15 $\mu$m.

The mixing ratio between the metal powder and M or M compound is set so that the amount of M in the final composition of the metal material is 0.01–3 wt %, preferably 0.03–2 wt %, and more preferably 0.05–0.5 wt %.

Examples of binders include polyethylene, polypropylene, ethylene-vinyl acetate copolymers, and other polyolefins; polymethyl methacrylate, polybutyl methacrylate, and other acrylic resins; polystyrene and other styrene-based resins; and polyvinyl chloride, polyamides, polyesters, polyethers, polyvinyl alcohol, copolymers thereof, and various other resins; as well as various waxes, paraffin, and the like. These binders can be used individually or as mixtures of two or more components described above.

It is preferable for the total amount in which such binders are added to be about 4 to 18 wt %, and more preferably about 4 to 10 wt %. If the amount is less than 4 wt %, fluidity is low during molding, thus leading to precluding or impairing injection molding or resulting in a green body with a nonuniform composition. On the other hand, if the amount is greater than 18 wt %, the coefficient of contraction during the sintering of the green body obtained by injection molding is increased, thereby tending to lower the dimensional accuracy and to increase the porosity over the range mentioned above.

Plasticizers, lubricants, antioxidants, debinding accelerators, surfactants, and various other additives may be added as needed in addition to the aforementioned metal powders, powder of M or M oxides and binders during compounding.

As for one example of the compounding conditions, a compounding temperature can be in the range from room temperature to about 150° C., and a compounding time can be about 60 to 180 min.

(2) Using the compound obtained in the above-described step (1) or pellets which are obtained by granulating the compound, injection molding is performed by an injection molding machine to obtain a green body having a shape of an artificial dental implant 1. Namely, a green body having a shape of the crown-fixing part 2 and a green body having a shape of the implanting part 3 are manufactured. In this case, the dimension of each green body is determined by taking shrinkage which will occur after the sintering process.

As for examples of the injection molding conditions, a material temperature is preferably set to be about 130 to 170° C. and more preferably about 150 to 160° C., an injection pressure is preferably set to be about 300 to 600 kgf/cm$^2$ and more preferably 300 to 400 kgf/cm$^2$ and a mold temperature is preferably set to be 10 to 20° C.

(3) A debinding treatment (binder removal treatment) is carried out for the green body obtained in the above-described step (2). This debinding treatment is accomplished by performing a heat treatment in a nonoxidizing atmosphere such as a vacuum or a reduced-pressure atmosphere (for examples $1\times10^{-1}$ to $1\times10^{-6}$ Torr).

In this case, it is preferred that the heat treatment conditions include a temperature of about 50 to 700° C. and a duration of about 8 to 72 hours, and it is more preferable that they include a temperature of about 50 to 650° C. and a duration of about 12 to 18 hours.

The debinding treatment (binder removal treatment) may be accomplished by dissolving prescribed components from the binder or additives with the aid of prescribed solvents (liquids, gases).

In this connection, it is to be noted that this process (3) may be omitted.

(4) Next, the green body thus obtained is sintered to manufacture a metallic sintered compact. Such a sintering process can be carried out two or more times.

The conditions adopted for such sintering are preferably a temperature of about 400 to 1400° C. and a time of about 10 to 26 hours, and more preferably a temperature of about 500 to 1350° C. and a time of about 15 to 18 hours.

In this case, it is preferable for the sintering atmosphere that the sintering is carried out under the nonoxidizing atmosphere, that is, a vacuum or a reduced-pressure atmosphere (preferably $1\times10^{-2}$ Torr, and more preferably $1\times10^{-2}$ to $1\times10^{-6}$ Torr), or in an inert gas such as argon gas, or other reducing atmosphere.

(5) In order to formed a coating layer 6 onto the outer surface of the metallic sintering compact, thermal spraying, plating, ion plating, sputtering, vapor deposition or CVD or other methods can be employed.

An artificial dental implant 1, that is a crown-fixing part 2 and an implanting part 3, formed from a metallic sintering compact is obtained via each of the processes indicated above.

According to the metal powder injection molding method as described above, there are no problems like casting defects and melt flow which were involved in the conventional casting method. Therefore, it is possible to manufacture artificial dental implants easily and in good yield.

Further, it is also possible to manufacture implants having complicated and fine shapes easily with good dimensional accuracy.

Furthermore, according to the metal powder injection molding method, since the M content can be controlled accurately, the composition of the metal material from which the artificial dental implant is made can be established as desired.

There is also a further advantage in that the nature of the pores, such as the pore size, and the porosity of the metal material from which the artificial dental implant is made can be adjusted as desired by controlling the type and amount of binder which is added, the conditions of the debinding treatment and the sintering conditions, for example.

Next, another structure for an artificial dental implant according to the present invention is described. Here, a description of the points which are in common with the artificial dental implant 1 described above is omitted, and just the main points of the difference therebetween are described.

Figure 4:
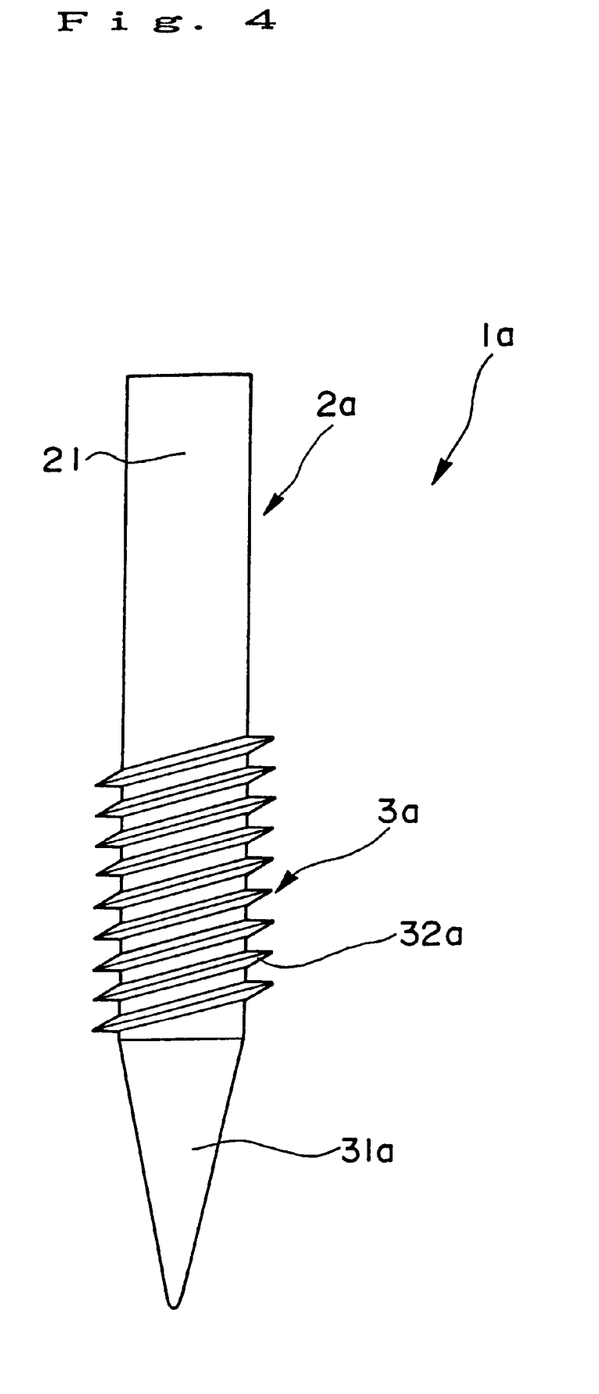
FIG. 4 is a cross sectional view which shows other example of the structure when an artificial dental implant of this invention is used as a cylinder-type artificial dental implant.

FIG. 4 is a cross sectional drawing which shows an example of the another structure when an artificial dental implant of this invention is applied to a cylinder-type artificial dental implant.

As shown in this drawing, the artificial dental implant 1*a* is formed with the implanting part 3*a* which is implanted in the bone tissue and the crown-fixing part 2*a* to which a crown, which is not shown in the drawing, is to be fixed. In this artificial dental implant 1*a*, the implanting part 3*a* and the crown-fixing part 2*a* are formed into an integral body.

The crown-fixing part 2*a* has a generally cylindrical shape and the implanting part 3*a* is formed on its bottom end (the lower side in FIG. 3).

The implanting part 3*a* is formed with a tip part 31*a* in which the diameter is gradually reduced towards the tip end thereof (the lower end in FIG. 4) and a screw (male thread) 32*a* which is formed on a portion above the base of the tip part 31*a* (the upper side in FIG. 4).

The conditions connected with the composition and porosity of the metal material from which the artificial dental implant 1*a* is made are the same as for the artificial dental implant 1 described above, so that a detailed description thereof is omitted here.

When fitting the artificial dental implant 1*a* to the patient, a screw (threaded hole) is formed in the prescribed position of the bone and then the implanting part 3*a* of the artificial dental implant 1*a* is screwed into this hole. That is to say, the implanting part 3*a* is implanted into the bone tissue. In this state, with the lapse of the prescribed period of time, bone tissue adheres around the implanting part 3*a* and the implanting part 3*a*, that is the artificial dental implant 1*a*, is fixed by bone tissue.

The artificial dental implant 1*a* of the type described above is made by the metal powder injection molding method. Since the metal powder injection molding method has already been described, a detailed description thereof is omitted here.

The artificial dental implant 1*a*, like the artificial dental implant 1 described above, has excellent bio-affinity, high strength and hardness, and it can be manufactured easily.

As described above, according to an artificial dental implant of the present invention, it is possible to provide an artificial dental implant which has excellent bio-affinity, which is light in weight and has adequate mechanical strength and hardness. In particular, if a coating layer is provided on the artificial dental implant as described above, the bio-affinity is further improved.

Further, since the artificial dental implants of this invention are made using the metal powder injection molding method, it is possible to manufacture artificial dental implants having complicated and delicate shapes easily and in good yield. Consequently, productivity is good and this is advantageous for mass production.

Moreover, since they are manufactured using the metal powder injection molding methods the conditions such as the composition and porosity, and the pore size, of the metal material from which the artificial dental implants are made can be set easily and precisely.

EXAMPLES

Hereinbelow, descriptions are made with reference to the examples of the artificial dental implants according to the the present invention.

(Example 1)

An artificial dental implant of the form shown in FIG. 1 was manufactured in the following way using the metal powder injection molding method.

First, Ti powder of average particle size 20 $\mu$m, 0.14 wt % CaO powder of average particle size 12 $\mu$m, and binder and other additives comprising 2.6 wt % ethylene glycidyl methacrylate—vinyl acetate copolymer, 1.6 wt % dibutyl phthalate, 2.8 wt % wax and 3.0 wt % styrene were mixed to obtain a mixture, and then thus obtained mixture was kneaded for 60 minutes at 130° C. using a kneading machine to obtain a compound.

Next, this compound was injection molded using an injection molding machine to obtain a green body of a crown-fixing part 2 having the shape indicated in FIG. 1. The molding conditions at this time were as follows: material temperature was 150° C., injection pressure was 400 kgf/cm$^2$ and mold temperature was 20° C.

Next, the thus obtained green body was subjected to a debinding treatment, in which the green body was heated from 60° C. to 450° C. over a period of 17 hours and then maintained at 450° C. for 1 hour under a reduced pressure of 1×10$^{-2}$ Torr, and then cooled to room temperature.

Next, the green body which had been subjected to the debinding treatment was heated from 600° C. to 1300° C. over a period of 15 hours and then maintained at 1300° C. for 3 hours under vacuum (5×10$^{-6}$ Torr), to obtain an implanting part 2 formed from a metal sintered compact in which Ti is contained as the main component.

Thereafter, Ti powder of average particle size 20 $\mu$m, 0.14 wt % CaO powder of average particle size 12 $\mu$m, and binder and other additives comprising 2.6 wt % ethylene glycidyl methacrylate—vinyl acetate copolymer, 1.6 wt % dibutyl phthalate, 2.8 wt % wax and 3.0 wt % styrene were mixed to obtain a mixture, and then thus obtained mixture was kneaded under atmosphere for 60 minutes at 130° C. using a kneading machine to obtain a compound.

Next, this compound was injection molded using an injection molding machine to obtain a green body of an implanting part 3 having the shape indicated in FIG. 1. The molding conditions at this time were as follows: material temperature was 150° C., injection pressure was 400 kgf/cm$^2$ and mold temperature was 20° C.

Next, the thus obtained green body was subjected to a debinding treatment, in which the green body was heated from 60° C. to 450° C. over a period of 17 hours and then maintained at 450° C. for 1 hour under a reduced pressure of $1\times10^{-2}$ Torr, and then cooled to room temperature.

Next, the green body which had been subjected to the debinding treatment was heated from 600° C. to 1300° C. over a period of 15 hours and then maintained at 1300° C. for 3 hours under vacuum ($5\times10^{-6}$ Torr), to obtain an implanting part 2 formed of a metal sintered compact in which Ti is contained as a main component.

In this ways an artificial dental implant of the form shown in FIG. 1 was obtained. The size and dimensions of each part of this artificial dental implant were as indicated below.

Length of Crown-fixing Part 2: 14.0 mm
Diameter of Head Part of Crown-fixing Part: 4.0 mm
Length of Implanting Part 3: 14.0 mm
External Size (Diameter) of Implanting Part 3: 4.0 mm (Example 2)

An artificial dental implant was manufactured in the same way as in Example 1 except that Ti powder of average particle size 20 $\mu$m, 0.21 wt % $Ca_3(PO_4)_2$ powder of average particle size 10 $\mu$m, and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound for the crown-fixing part 2; and that Ti powder of average particle size 20 $\mu$m, 0.21 wt % $Ca_3(PO_4)_2$ powder of average particle size 10 $\mu$m, and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound for the implanting part 3.

(Example 3)

An artificial dental implant was manufactured in the same way as in Example 1 except that Ti powder of average particle size 20 $\mu$m, 0.23 wt % $CaSiO_3$ powder of average particle size 8 $\mu$m, and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound for the crown-fixing part 2; and that Ti powder of average particle size 20 $\mu$m, 0.23 wt % $CaSiO_3$ powder of average particle size 8 $\mu$m, and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound for the implanting part 3.

(Example 4)

An artificial dental implant was manufactured in the same way as in Example 1 except that Ti powder of average particle size 20 $\mu$m, 0.23 wt % $CaSiO_3$ powder of average particle size 8 $\mu$m, 0.09 wt % $P_2O_3$ powder of average particle size 10 $\mu$m and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound for the crown-fixing part 2; and that Ti powder of average particle size 20 $\mu$m, 0.23 wt % $CaSiO_3$ powder of average particle size 8 $\mu$m, 0.09 wt % $P_2O_3$ powder of average particle size 10 $\mu$m and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound for the implanting part 3.

(Example 5)

An artificial dental implant was manufactured in the same way as in Example 4 except that Ti—6 wt % of Al—4 wt % of V alloy powder having average particle size 20 $\mu$m was used instead of Ti powder.

(Example 6)

An artificial dental implant was manufactured in the same way as in Example 4 except that Ti powder of average particle size 20 $\mu$m, 0.12 wt % $CaSiO_3$ powder of average particle size 8 $\mu$m, 0.05 wt % $P_2O_3$ powder of average particle size 10 $\mu$m and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound for the crown-fixing part 2; and that Ti powder of average particle size 20 $\mu$m, 0.30 wt % $CaSiO_3$ powder of average particle size 8 $\mu$m, 0.15 wt % $P_2O_3$ powder of average particle size 10 $\mu$m and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound for the implanting part 3.

(Example 7)

An artificial dental implant was manufactured in the same way as in Example 1 except that a coating layer which is formed of CaO by thermal spraying so as to have a thickness of 60 $\mu$m is formed onto the outer surfaces of the crown-fixing part 2 and the implanting part 3, respectively.

(Example 8)

An artificial dental implant was manufactured in the same way as in Example 2 except that a coating layer which is formed of $Ca_3(PO_4)_2$ by thermal spraying so as to have a thickness of 60 $\mu$m is formed onto the outer surfaces of the crown-fixing part 2 and the implanting part 3, respectively.

(Example 9)

An artificial dental implant was manufactured in the same way as in Example 3 except that a coating layer which is formed of $CaSiO_3$ by thermal spraying so as to have a thickness of 60 $\mu$m is formed onto the outer surfaces of the crown-fixing part 2 and the implanting part 3, respectively.

(Example 10)

An artificial dental implant was manufactured in the same way as in Example 4 except that a coating layer which is formed of $CaSiO_3$ and $P_2O_3$ by thermal spraying so as to have a thickness of 60 mm is formed onto the outer surfaces of the crown-fixing part 2 and the implanting part 3, respectively.

(Example 11)

An artificial dental implant was manufactured in the same way as in Example 5 except that a coating layer which is formed of $CaSiO_3$ and $P_2O_3$ by thermal spraying so as to have a thickness of 60 $\mu$m is formed onto the outer surfaces of the crown-fixing part 2 and the implanting part 3, respectively.

(Example 12 )

An artificial dental implant was manufactured in the same way as in Example 6 except that a coating layer which is formed of $CaSiO_3$ and $P_2O_3$ by thermal spraying so as to have a thickness of 60 $\mu$m is formed onto the outer surfaces of the crown-fixing part 2 and the implanting part 3, respectively.

(Example 13)

An artificial dental implant of the form shown in FIG. 4 was manufactured in the following way using the metal powder injection molding method.

First, Ti powder of average particle size 20 $\mu$m, 0.14 wt % CaO powder of average particle size 12 $\mu$m, and binder and other additives comprising 2.6 wt % ethylene glycidyl methacrylate—vinyl acetate copolymer, 1.6 wt % dibutyl phthalate, 2.8 wt % wax and 3.0 wt % styrene were mixed to obtain a mixtures and then thus obtained mixture was kneaded under atmosphere for 60 minutes at 130° C. using a kneading machine to obtain a compound.

Next, this compound was injection molded using an injection molding machine to obtain a green body of an artificial dental implant 1a having the shape indicated in FIG. 4. The molding conditions at this time were as follows: material temperature was 150° C., injection pressure was 400 kgf/cm$^2$ and mold temperature was 20° C.

Next, the thus obtained green body was subjected to a debinding treatment, in which the green body was heated from 60° C. to 450° C. over a period of 17 hours and then maintained at 450° C. for 1 hour under a reduced pressure of 1×10$^{-2}$ Torr, and then cooled to room temperature.

Next, the green body which had been subjected to the debinding treatment was heated from 600° C. to 1200° C. over a period of 15 hours and then sintered at 1200° C. for 3 hours under vacuum (5×10$^{-6}$ Torr), to obtain an artificial dental implant 1a formed of a metal sintered compact in which Ti is contained as a main component.

The sizes and dimensions of each part of this artificial dental implant were as indicated below.

Length of Artificial Dental Implant 1a: 16.0 mm
Diameter of Head Part of
Artificial Dental Implant 1a: 4.0 mm (Example 14)
An artificial dental implant was manufactured in the same way as in Example 13 except that Ti powder of average particle size 20 μm, 0.21 wt % Ca$_3$(PO$_4$)$_2$ powder of average particle size 10 μm, and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound.

(Example 15)
An artificial dental implant was manufactured in the same way as in Example 13 except that Ti powder of average particle size 20 μm, 0.23 wt % CaSiO$_3$ powder of average particle size 8 μm, and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound.

(Example 16)
An artificial dental implant was manufactured in the same way as in Example 13 except that Ti powder of average particle size 20 μm, 0.23 wt % CaSiO$_3$ powder of average particle size 8 μm, 0.09 wt % P$_2$O$_3$ powder of average particle size 10 μm and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound.

(Example 17)
An artificial dental implant was manufactured in the same way as in Example 16 except that Ti—6 wt % of Al—4 wt % of V alloy powder having average particle size 20 μm was used instead of Ti powder.

(Example 18)
An artificial dental implant was manufactured in the same way as in Example 13 except that a coating layer which is formed of CaO by thermal spraying so as to have a thickness of 60 μm is formed onto the outer surfaces of the artificial dental implant.

(Example 19)
An artificial dental implant was manufactured in the same way as in Example 14 except that a coating layer which is formed of Ca$_3$(PO$_4$)$_2$ by thermal spraying so as to have a thickness of 60 μm is formed onto the outer surfaces of the artificial dental implant.

(Example 20)
An artificial dental implant was manufactured in the same way as in Example 15 except that a coating layer which is formed of CaSiO$_3$ by thermal spraying so as to have a thickness of 60 μm is formed onto the outer surfaces of the artificial dental implant.

(Example 21)
An artificial dental implant was manufactured in the same way as in Example 16 except that a coating layer which is formed of CaSiO$_3$ and P$_2$O$_3$ by thermal spraying so as to have a thickness of 60 μm is formed onto the outer surfaces of the artificial dental implant.

(Example 22)
An artificial dental implant was manufactured in the same way as in Example 17 except that a coating layer which is formed of CaSiO$_3$ and P$_2$O$_3$ by thermal spraying so as to have a thickness of 60 μm is formed onto the outer surfaces of the artificial dental implant.

(Comparative Example 1)
An artificial dental implant of the form shown in FIG. 1 was manufactured using a casting method instead of the metal injection molding method.

(Comparative Example 2)
An artificial dental implant was manufactured in the same way as in Example 1 except that Ti powder of average particle size 20 μm, and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound.

(Comparative Example 3)
An artificial dental implant was manufactured in the same way as in Example 13 except that Ti powder of average particle size 20 μm, 14 wt % CaO powder of average particle size 12 μm, and binder and additives comprising 2.6 wt % ethyleneglycidyl methacrylate—vinyl acetate copolymer, 1.6 wt % dibutyl phthalate, 2.8 wt % wax and 3.0 wt % styrene were used as the raw materials for the compound.

<Composition of the Metal Material>
The composition of the metal powder (Ti, Ca, P and Si contents) was analyzed using an analyzing apparatus T-300 manufactured by the Nippon Denshi Co., Ltd. for each of the artificial dental implants of Examples 1 to 22 and Comparative Examples 1 to 3. The results are shown in the attached Tables 1 and 2.

<Conditions Relating to Pores>
The surfaces and cross sectional surfaces of the artificial dental implants of Examples 1 to 22 and Comparative Examples 1 to 3 were photographed through an electron microscope. Then, the average pore diameter was obtained with reference to each electron micrograph, and the porosity was obtained from the density ratio. The results are shown in the attached Table 3.

<Tests>
The artificial dental implants of Examples 1 to 22 and Comparative Examples 1 to 3 were evaluated in terms of each of the items 1 to 4 indicated below (sample number in each case=10). The results are shown in the attached Tables 4 and 5.

1. Mechanical Strength (Transverse Rupture Strength)
(Method of Measurement)
The transverse rupture strength was measured in accordance with JIS Z 2203 using transverse rupture flex resistance strength specimens after sintering.

2. Hardness
(Method of Measurement)
The Vickers hardness Hv (load 5 grams) was measured in accordance with JIS Z 2244.

3. Bio-affinity (Method of Evaluation)

Specimens (thickness 1 mm×length 2 mm×width 2 mm) were prepared under the same conditions as each of the Examples and Comparative Examples. Then, about 2×10$^4$ osteoblast cells were introduced into a 35 mm Petri dish and each specimen was placed on top of the cells, 10 mM B-glycelophosphate was added and the dishes were incubated for 21 days. After incubation, staining was carried out with Alizarin Red and the extent of the multiplication of the cells was compared using image analyzing apparatus.

The cells which had been stained red were osteoblasts. A higher quantity of these cells indicates superior bio-affinity. The result was indicated by ⊚ when the area occupied by these cells was three fifths or more of the area of the Petri dish, by ◯ when it was more than one fifth but less than three fifths, and x when it was less than one fifth.

4. Adhesion (Method of Evaluation)

Specimens each having a coating layer were made under the same conditions as those in Examples 7 to 12 and 18 to 22. Each specimen was bent through 90° and it was observed in this condition.

Figure 5:
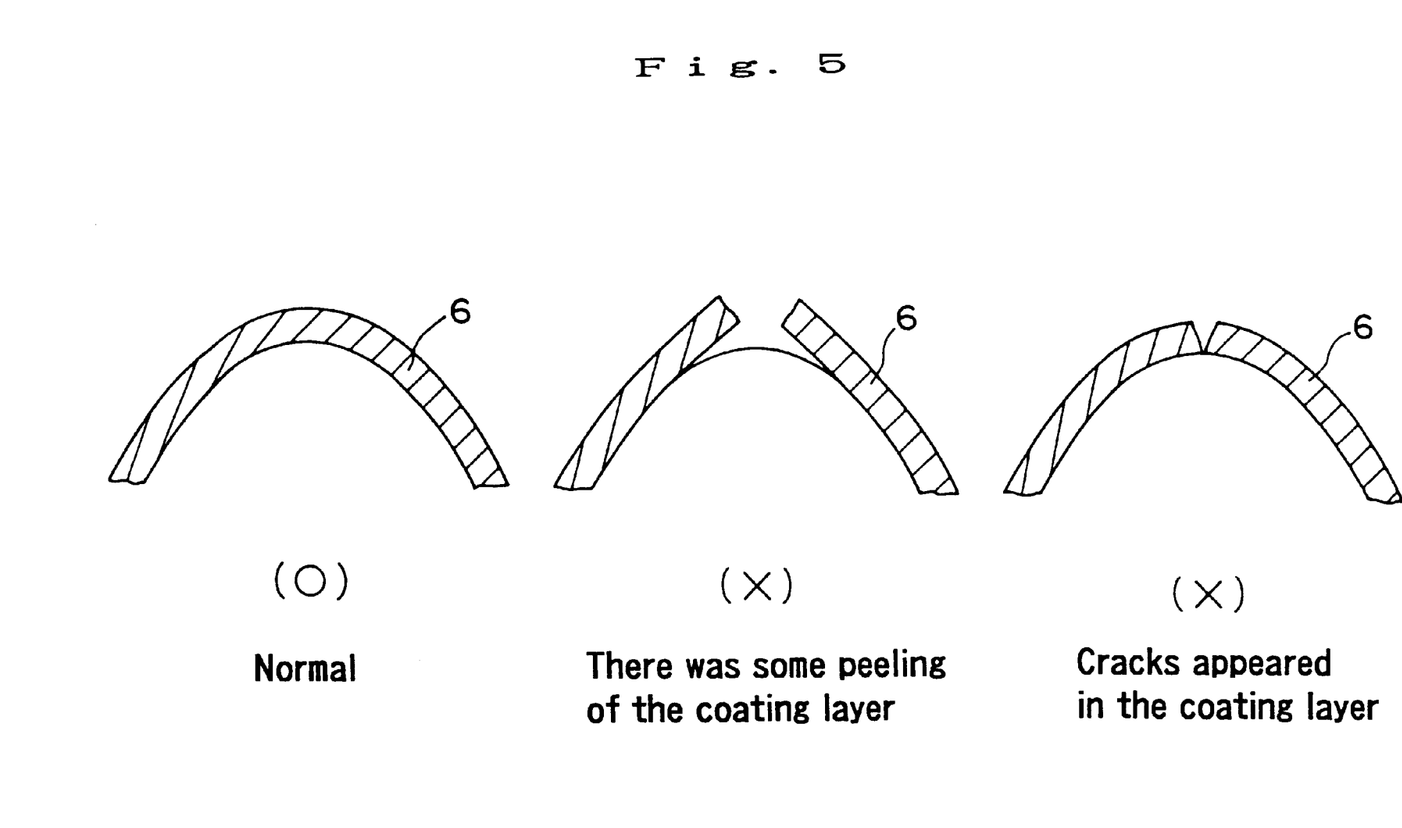
FIG. 5 is an illustration which shows the evaluation standards for attachment of a coating layer.

As shown in FIG. 5, those which were normal are indicated by ◯, and those where there was some peeling of the coating layer 6 or where cracks appeared in the coating layer 6 are indicated by x, which are shown in the attached Table 4.

<Discussion of the Test Results>

As is shown in the attached Tables 4 and 5, the artificial dental implants of Examples 1 to 22 all had high mechanical strength (transverse rupture strength) and hardness, and excellent bio-affinity. The artificial dental implants of Examples 7 to 12 and 18 to 22 which had a coating layer in particular had especially good bio-affinity, and the adhesion of the coating layer was good.

On the other hand, since the artificial dental implants of Comparative Examples 1 and 2 did not have M (M being at least one selected from Ca, P and Si) included in the metal material, the bio-affinity was poor.

Furthermore, since the artificial dental implant of Comparative Example 3 had a large Ca content in the metal material, the mechanical strength and hardness were reduced.

In the above description, artificial dental implants of this invention have been described with reference to the structures shown in the drawings, but the invention is not limited to these structures.

For example, the form of the artificial dental implant is not limited to those shown in the drawings, and the shape of the head of the crown-fixing part may be that of a square pillar.

Furthermore, in this invention, at least a part of the portion which defines the outer surface of the implanting part and or the crown-fixing part should be made from a metal material which contains Ti as a main component and 0.01 to 3 wt % M (where M is at least one selected from Ca, P and Si).

Furthermore, in the present invention a prescribed concentration gradient of M in the metal material can be established from the surface to the inside or along the axial direction.

Furthermore, in this invention the aforementioned coating layer may be formed either on only the crown-fixing part or on only the implanting part.

Finally, it is to be noted that the present invention is not limited to the embodiments and the examples described above, and any changes and modifications can be made without departing from the scope and spirit of the present invention which are defined by the following claims.

TABLE 1

| | Crown-Fixing Part [wt %] | | | | Implanting Part [wt %] | | | | Coating Layer [wt %] | | | |
|---|---|---|---|---|---|---|---|---|---|---|---|---|
| | Base Metal | Ca | P | Si | Base Metal | Ca | P | Si | Ca | P | Si | O |
| Example 1 | Ti | 0.10 | — | — | Ti | 0.10 | — | — | No Coating Layer | | | |
| Example 2 | Ti | 0.08 | 0.04 | — | Ti | 0.08 | 0.04 | — | No Coating Layer | | | |
| Example 3 | Ti | 0.08 | — | 0.06 | Ti | 0.08 | — | 0.06 | No Coating Layer | | | |
| Example 4 | Ti | 0.08 | 0.05 | 0.06 | Ti | 0.08 | 0.05 | 0.06 | No Coating Layer | | | |
| Example 5 | Ti-Alloy | 0.08 | 0.05 | 0.06 | Ti-Alloy | 0.08 | 0.05 | 0.06 | No Coating Layer | | | |
| Example 6 | Ti | 0.04 | 0.03 | 0.03 | Ti | 0.10 | 0.09 | 0.07 | No Coating Layer | | | |
| Example 7 | Ti | 0.10 | — | — | Ti | 0.10 | — | — | 71 | — | — | 29 |
| Example 8 | Ti | 0.08 | 0.04 | — | Ti | 0.08 | 0.04 | — | 39 | 20 | — | 41 |
| Example 9 | Ti | 0.08 | — | 0.06 | Ti | 0.08 | — | 0.06 | 34 | — | 24 | 42 |
| Example 10 | Ti | 0.08 | 0.05 | 0.06 | Ti | 0.08 | 0.05 | 0.06 | 18 | 27 | 12 | 43 |
| Example 11 | Ti-Alloy | 0.08 | 0.05 | 0.06 | Ti-Alloy | 0.08 | 0.05 | 0.06 | 18 | 27 | 12 | 43 |
| Example 12 | Ti | 0.04 | 0.03 | 0.03 | Ti | 0.10 | 0.09 | 0.07 | 18 | 27 | 12 | 43 |

TABLE 2

| | Crown-Fixing Part [wt %] | | | | Implanting Part [wt %] | | | | Coating Layer [wt %] | | | |
|---|---|---|---|---|---|---|---|---|---|---|---|---|
| | Base Metal | Ca | P | Si | Base Metal | Ca | P | Si | Ca | P | Si | O |
| Example 13 | Ti | 0.10 | — | — | Ti | 0.10 | — | — | No Coating Layer | | | |
| Example 14 | Ti | 0.08 | 0.04 | — | Ti | 0.08 | 0.04 | — | No Coating Layer | | | |
| Example 15 | Ti | 0.08 | — | 0.06 | Ti | 0.08 | — | 0.06 | No Coating Layer | | | |
| Example 16 | Ti | 0.08 | 0.05 | 0.06 | Ti | 0.08 | 0.05 | 0.06 | No Coating Layer | | | |
| Example 17 | Ti-Alloy | 0.08 | 0.05 | 0.06 | Ti-Alloy | 0.08 | 0.05 | 0.06 | No Coating Layer | | | |
| Example 18 | Ti | 0.10 | — | — | Ti | 0.10 | — | — | 71 | — | — | 29 |
| Example 19 | Ti | 0.08 | 0.04 | — | Ti | 0.08 | 0.04 | — | 39 | 20 | — | 41 |
| Example 20 | Ti | 0.08 | — | 0.05 | Ti | 0.08 | — | 0.06 | 34 | — | 24 | 42 |
| Example 21 | Ti | 0.08 | 0.05 | 0.06 | Ti | 0.08 | 0.05 | 0.06 | 18 | 27 | 12 | 43 |
| Example 22 | Ti-Alloy | 0.08 | 0.05 | 0.06 | Ti-Alloy | 0.08 | 0.05 | 0.06 | 18 | 27 | 12 | 43 |

TABLE 2-continued

| | Crown-Fixing Part [wt %] | | | | Implanting Part [wt %] | | | | Coating Layer [wt %] | | | |
|---|---|---|---|---|---|---|---|---|---|---|---|---|
| | Base Metal | Ca | P | Si | Base Metal | Ca | P | Si | Ca | P | Si | O |
| Comp.Ex. 1 | Ti | — | — | — | Ti | — | — | — | No Coating Layer | | | |
| Comp.Ex. 2 | Ti | — | — | — | Ti | — | — | — | No Coating Layer | | | |
| Comp.Ex. 3 | Ti | 10.00 | — | — | Ti | 10.00 | — | — | No Coating Layer | | | |

TABLE 3

| | Average Diameter of Pores [μm] | | Porosity [vol %] | | | Average Diameter of Pores [μm] | | Porosity [vol %] | |
|---|---|---|---|---|---|---|---|---|---|
| | Crown-fixing Part | Implanting Part | Crown-fixing Part | Implanting Part | | Crown-fixing Part | Implanting Part | Crown-fixing Part | Implanting Part |
| Example 1 | 17 | 36 | 1.9 | 9.6 | Example 14 | 25 | 26 | 5.8 | 6.4 |
| Example 2 | 16 | 31 | 1.8 | 8.8 | Example 15 | 25 | 25 | 6.2 | 5.9 |
| Example 3 | 17 | 31 | 2.0 | 8.5 | Example 16 | 27 | 26 | 5.7 | 6.1 |
| Example 4 | 15 | 35 | 1.7 | 9.2 | Example 17 | 28 | 27 | 6.1 | 6.2 |
| Example 5 | 18 | 42 | 1.9 | 10.3 | Example 18 | 26 | 26 | 5.9 | 6.3 |
| Example 6 | 16 | 38 | 1.8 | 9.9 | Example 19 | 27 | 25 | 6.2 | 6.5 |
| Example 7 | 16 | 37 | 1.9 | 8.9 | Example 20 | 26 | 27 | 5.5 | 6.1 |
| Example 8 | 17 | 36 | 2.0 | 9.1 | Example 21 | 28 | 29 | 5.9 | 6.6 |
| Example 9 | 18 | 37 | 1.9 | 9.2 | Example 22 | 27 | 25 | 6.2 | 6.2 |
| Example 10 | 19 | 35 | 1.9 | 9.0 | Comp.Ex. 1 | 125 | 131 | 3.2 | 2.9 |
| Example 11 | 17 | 33 | 1.8 | 8.8 | Comp.Ex. 2 | 18 | 33 | 1.8 | 9.2 |
| Example 12 | 18 | 34 | 1.8 | 8.9 | Comp.Ex. 3 | 15 | 30 | 1.7 | 8.3 |
| Example 13 | 26 | 25 | 5.2 | 5.9 | | | | | |

TABLE 4

| | Transverse Rupture Strength [kg/mm$^2$] | | Vickers Hardness Hv | | | |
|---|---|---|---|---|---|---|
| | Crown-fixing Part | Implanting Part | Crown-fixing Part | Implanting Part | Bio-Affinity | Adhesion |
| Example 1 | 71 | 52 | 230 | 225 | ○ | — |
| Example 2 | 73 | 49 | 245 | 231 | ○~◉ | — |
| Example 3 | 72 | 55 | 233 | 220 | ○~◉ | — |
| Example 4 | 70 | 53 | 236 | 221 | ○~◉ | — |
| Example 5 | 93 | 78 | 382 | 335 | ○~◉ | — |
| Example 6 | 71 | 54 | 233 | 220 | ○~◉ | — |
| Example 7 | 69 | 52 | 241 | 218 | ◉ | ○ |
| Example 8 | 73 | 52 | 235 | 230 | ◉ | ○ |
| Example 9 | 72 | 53 | 229 | 215 | ◉ | ○ |
| Example 10 | 70 | 48 | 231 | 223 | ◉ | ○ |
| Example 11 | 71 | 52 | 241 | 218 | ◉ | ○ |
| Example 12 | 70 | 51 | 243 | 228 | ◉ | ○ |

TABLE 5

| | Transverse Rupture Strength [kg/mm$^2$] | | Vickers Hardness Hv | | | |
|---|---|---|---|---|---|---|
| | Crown-fixing Part | Implanting Part | Crown-fixing Part | Implanting Part | Bio-Affinity | Adhesion |
| Example 13 | 63 | 63 | 220 | 220 | ○ | — |
| Example 14 | 65 | 65 | 221 | 221 | ○~◉ | — |
| Example 15 | 63 | 63 | 225 | 225 | ○~◉ | — |
| Example 16 | 61 | 61 | 219 | 219 | ○~◉ | — |
| Example 17 | 89 | 89 | 368 | 368 | ○~◉ | — |
| Example 18 | 62 | 62 | 218 | 218 | ◉ | ○ |
| Example 19 | 63 | 63 | 223 | 223 | ◉ | ○ |
| Example 20 | 63 | 63 | 220 | 220 | ◉ | ○ |
| Example 21 | 68 | 68 | 224 | 224 | ◉ | ○ |
| Example 22 | 67 | 67 | 219 | 219 | ◉ | ○ |
| Comp.Ex. 1 | 75 | 73 | 250 | 241 | X | — |
| Comp.Ex. 2 | 68 | 52 | 241 | 220 | X | — |
| Comp.Ex. 3 | 34 | 31 | 199 | 205 | ○ | — |

What is claimed is:

1. Artificial dental implant, comprising:
   an implanting part which is to be implanted in bone tissue, said implanting part having a portion defining an outer surface thereof and the porosity of said implanting part is from 5 to 15 vol %; and
   a crown-fixing part to which a crown is to be fixed;
   wherein both said implanting part and said crown-fixing part are manufactured using a metal powder injection molding method, and at least a part of said portion of said implanting part is formed with a metal material which contains Ti as a main component and 0.01 to 3 wt % of M (where M is at least one selected from the group comprising Ca, P and Si).

2. The artificial dental implant as claimed in claim 1, wherein the metal material of said at least a part of said portion of said implanting part includes 0.01 to 1 wt % of Ca.

3. The artificial dental implant as claimed in claim 1, wherein the metal material of said at least a part of said portion of said implanting part includes 0.01 to 0.5 wt % of P.

4. The artificial dental implant as claimed in claim 1, wherein the metal material of said at least a part of said portion of said implanting part includes 0.01 to 0.5 wt % of Si.

5. The artificial dental implant as claimed in claim 1, wherein the porosity of said crown-fixing part is equal to or less than 3 vol %.

6. The artificial dental implant as claimed in claim 1, further comprising a coating layer which covers the outer surface of said implanting part, said coating layer being formed of a metal material containing M (where M is at least one selected from the group comprising Ca, P and Si).

7. The artificial dental implant as claimed in claim 6, wherein the M content in said coating layer is greater than the M content in said at least a part of said portion of said implanting part.

8. The artificial dental implant as claimed in claim 6, wherein said coating layer is formed of a porous material.

9. The artificial dental implant as claimed in claim 1, wherein said implanting part and said crown-fixing part are formed into an integral body.

10. Artificial dental implant, comprising:
    an implanting part which is to be implanted in bone tissue and which is manufactured using a metal powder injection molding method, said implanting part having a portion defining an outer surface thereof and the porosity of said implanting part is from 5 to 15 vol %; and
    a crown-fixing part to which a crown is to be fixed and which is manufactured using the metal powder injection molding method, said crown-fixing part adapted to be engaged with said implanting part when used,
    wherein at least a part of said portion of said implanting part is formed with a metal material which contains Ti as a main component and 0.01 to 3 wt % of M (where M is at least one selected from the group comprising Ca, P and Si).

11. The artificial dental implant as claimed in claim 10, wherein the metal material of said at least a part of said portion of said implanting part includes 0.01 to 1 wt % of Ca.

12. The artificial dental implant as claimed in claim 10, wherein the metal material of said at least a part of said portion of said implanting part includes 0.01 to 0.5 wt % of P.

13. The artificial dental implant as claimed in claim 10, wherein the metal material of said at least a part of said portion of said implanting part includes 0.01 to 0.5 wt % of Si.

14. The artificial dental implant as claimed in claim 10, wherein the porosity of said crown-fixing part is equal to or less than 3 vol %.

15. The artificial dental implant as claimed in claim 10, further comprising a coating layer which covers the outer surface of said implanting part, said coating layer being formed of a metal material containing M (where M is at least one selected from the group comprising Ca, P and Si).

16. The artificial dental implant as claimed in claim 15, wherein the M content in said coating layer is greater than the M content in said at least a part of said portion of said implanting part.

17. The artificial dental implant as claimed in claim 15, wherein said coating layer is formed of a porous material.

18. The artificial dental implant as claimed in claim 10, wherein the porosity of said implanting part is higher than the porosity of said crown-fixing part.

19. The artificial dental implant as claimed in claim 10, wherein the M content of said implanting part is greater than the M content (where M is at least one selected from the group comprising Ca, P and Si) of said crown-fixing part.

20. Artificial dental implants comprising:
    an implanting part which is to be implanted in bone tissue and which is manufactured using a metal powder injection molding method, said implanting part having a portion defining an outer surface thereof, in which at least a part of said portion of said implanting part being formed with a metal material which contains Ti as a main component and 0.01 to 3 wt % of M (where M is at least one selected from the group comprising Ca, P and Si); and
    a crown-fixing part to which a crown is to be fixed and which is manufactured using the metal powder injection molding method, said crown-fixing part adapted to be engaged with said implanting part when used,
    wherein the porosity of said implanting part is higher than the porosity of said crown-fixing part, and the M content of said implanting part is greater than the M content (where M is at least one selected from the group comprising Ca, P and Si) of said crown-fixing part.

21. The artificial dental implant as claimed in claim 20, further comprising a coating layer which covers the outer surface of said implanting part, said coating layer being formed of a metal material containing M (where M is at least one selected from the group comprising Ca, P and Si).

* * * * *